United States Patent [19]

Brown

[11] Patent Number: 5,042,987
[45] Date of Patent: Aug. 27, 1991

[54] METHOD FOR REDUCING SCALP STAINING IN HAIR DYEING PROCESSES INVOLVING A METAL ION PRETREATMENT STEP

[75] Inventor: Keith Brown, New Canaan, Conn.

[73] Assignee: Clairol, Inc., New York, N.Y.

[21] Appl. No.: 580,694

[22] Filed: Sep. 11, 1990

[51] Int. Cl.⁵ ................................................. A61K 7/13
[52] U.S. Cl. ........................................... 8/406; 8/408; 8/429
[58] Field of Search ...................... 8/405, 406–424, 8/429

[56] References Cited

U.S. PATENT DOCUMENTS 4,904,274 2/1990 Schultz et al. .......................... 8/406
4,971,596 11/1990 Grallien .................................. 8/424

FOREIGN PATENT DOCUMENTS 2028818 12/1970 Fed. Rep. of Germany.

OTHER PUBLICATIONS

Zviak, The Science of Hair Care, Marcel Dekken, Inc., ISBN 0-8247-7378-0, 1986, pp. 263-281.

Primary Examiner—Paul Lieberman
Assistant Examiner—J. E. Darland
Attorney, Agent, or Firm—Morton S. Simon

[57] ABSTRACT

Hair on a live head is treated with metal ion in a pretreatment step then subjected to an oxidative or autooxidative dyeing step in which scalp staining occurs. Between the pretreatment step and the dyeing step the scalp of the live head is subjected to vigorous massage, rubbing, combing or brushing for a time sufficient to reduce scalp staining, or sufficient time is permitted to elapse between the pretreatment step of the dyeing step to reduce scalp staining, or a combination of these two procedures is employed.

4 Claims, No Drawings

METHOD FOR REDUCING SCALP STAINING IN HAIR DYEING PROCESSES INVOLVING A METAL ION PRETREATMENT STEP

BACKGROUND OF INVENTION

1. Field of Invention

The present invention relates to a method for reducing scalp staining when metal ion pretreatments are used to activate dyeing processes on live heads.

2. Description of the Prior Art

The use of metal ion treatments to activate a variety of hair coloring processes is know in the art. For example Ger. 2,028,818 discloses accelerated oxidative dyeing by use of a pretreatment containing one of a variety of metal ions. Autooxidative dyeing systems which usually contain dye ingredients, such as pyrogallol, 1,2,-4-trihydroxybenzene or other readily oxidized phenolics, are also claimed to be activated by metal ions (see for example U.S. Pat. No. 629,231).

Natural dyes and natural dye precursors that are known in the art as being capable of being activated by metal ions, include: indolic compounds (U.S. Pat. Nos. 2,934,296, and 3,194,734 and GB 797,174), logwood extracts (U.S. Pat. No. 4,801,302), henna and other quinone dyes (Czech 142,851).

Commercial exploitation of such dyeing processes is severely restricted by the fact that they have a number of significant drawbacks. The foremost drawback is the unacceptable amount of scalp staining produced when these dyeing systems are used on live heads. The affinity of metal ions for hair keratin and skin is quite similar. Therefore, a significant fraction of the metal ion applied is adsorbed by the scalp skin. Metal ion adsorbed by skin and metal adsorbed by hair have equivalent reactivity in the dyeing processes. Thus, a significant amount of color is produced on the scalp during hair dyeing. This is undesirable. With permanent dyes, i.e. dyes that are not readily removed by shampooing, the scalp coloration that is produced can last for a considerable time. Thus prior art processes are unsatisfactory.

The present invention provides an improvement in a process for dyeing hair on a live head wherein the hair is treated with metal ion in a pretreatment step to accelerate subsequent dyeing of the hair and the treated hair is then subjected to an oxidative or autooxidative dyeing step. The improvement comprises, (a) between the pretreatment step and the dyeing step the scalp of said live head is subjected to vigorous massage, rubbing, combing or brushing, for a time sufficient to reduce staining of the scalp occasioned by the dyeing step; or (b) sufficient time is permitted to elapse between the pretreatment step and the dyeing step to reduce staining of the scalp occasioned by the dyeing step; or (c) between the pretreatment step and he dyeing step the scalp of said live head is subjected to vigorous massage, rubbing, combing or brushing and time is permitted to elapse between the pretreatment step and the dyeing step, the duration of the massage rubbing, combing or brushing coupled with the duration of the elapsed time between the pretreatment and dyeing steps being sufficient to reduce staining of the scalp occasioned by the dyeing step.

SUMMARY OF THE INVENTION

The present inventor found that the heretofore described undesirable scalp staining can surprisingly and unexpectedly be almost entirely eliminated by allowing a time period to elapse between application of the metal ion and application of the dye. The duration of the time period is dependent on a number of factors. Although the instant inventor does not wish to be restricted by the following hypothesis, it is believed that during such elapsed time period metal ion adsorbed onto the surface of the skin is desquamated along with the skin. Sufficient time must elapse for the natural process of desquamation to remove most of the active metal ions from the scalp skin. Generally, a period of at least 24 hours, more preferably a period of a least 48, hours of elapsed time is adequate to reduce scalp staining to an acceptable level. As a practical matter, a period of 24 hours to less than 48 hours elapsed time will suffice but a period of 48 hours to 72 hours is optimal. During this elapsed time, the metal ion adsorbed onto the hair has not lost any of its activity with respect to activation of color formation.

Surprisingly and unexpectedly the present inventor has found that the time delay called for by the method of the instant invention is significantly reduced by processes which accelerate scalp desquamation. A vigorous shampooing after application of the metal ion-containing formulation allows the user to dye his or her hair using substantially less elapsed time between the pretreatment step and the dyeing step while obtaining a considerable reduction in concurrent scalp staining. For certain oxidative dyes a vigorous shampooing, after application of the metal ion-containing formulation allows the user to dye his or her hair substantially immediately afterward with a considerable reduction in concurrent scalp staining. Other processes which substantially decrease the duration of the time period required between the application of the metal ion and the application of the dye include vigorous massaging, rubbing combing and brushing of the scalp hair. Advantageously, none of these processes change the degree of dye take on the hair.

The method of the present invention offers many advantages. Its primary advantage is that it allows a hair colorist to exploit the advantages of metal ion pretreatment for hair dyeing systems, i.e. faster development of color and more intense color formation, while substantially avoiding the usual concurrent problem of scalp staining.

EXAMPLES

Example 1

(a) A live head of gray hair was rinsed with a solution of 1 g of ferrous sulfate heptahydrate in 100 ml of water previously adjusted to pH 9.5. with a citric acid-ammonia mixture.

After a water rinse, a commercially available oxidative dye composition (NICE 'N EASY ® Shade 120—Dark Brown) was prepared following the package instructions then rubbed into the hair and left on for five minutes. It was then shampooed off. The hair was dyed dark brown. The scalp also showed strong staining, especially at the hair and part lines. The staining was not removed by shampooing.

(b) The procedure of part (a) of this Example 1 was repeated on another live head of gray hair, but this time 24 hours were allowed to elapse between the metal ion treatment step and the dyeing step. This time scalp staining was vastly less. Moreover, visible staining was readily removed by a shampooing.

Example 2

(a) A live head of gray hair was shampooed twice with a solution of copper sulfate (1 g) in a 10% solution of sodium lauryl sulfate in water (100 ml).

After thorough rinsing, a freshly prepared solution of 5,6-dihydroxyindole (1 g) in water (100 ml) was spread through the hair and left on for ten minutes. After rinsing and shampooing, the hair was dyed a deep black. However, the scalp hair and part lines were also badly stained black. The staining was not removed by shampooing or rubbing.

(b) The procedure of part (a) of this Example 2 was repeated on another live head of gray hair, however, 24 hours were allowed to elapse between the metal ion and dihydroxyindole treatment steps. This time the scalp was almost free of any discoloration.

(c) A third head of live gray hair was dyed as described in part (b) of this Example 2 however, during the 24 hour interval which elapsed between the metal ion and dihydroxyindole treatment steps the hair was vigorously shampooed with a commercial shampoo (CLAIROL CONDITION ® for Normal Hair). After dyeing, there was no visible scalp staining.

Example 3

(a) A live head of white hair was rinsed with a solution of manganese chloride (2 g) in (100 ml). The solution had been adjusted to pH 10 with monoethanolamine.

After rinsing, a commercial auto-oxidative dye (CLAIROL OPTION GRADUAL ®—Dark Brown: active ingredient 1,2,4-benzenetriol) was rubbed into the hair and left on for ten minutes. After rinsing and shampooing, the hair was colored dark brown and the scalp was heavily stained. The scalp staining could not be removed by shampooing or rubbing.

(b) A second head of live white hair was treated as described in part (a) of this Example 3, except that the metal ion solution was immediately followed by a vigorous shampoo with CLAIROL's CONDITION ® Shampoo for Normal Hair.

After rinsing out the shampoo, the head was immediately dyed. This was followed by a rinse. After rinsing, almost no scalp staining was evident.

It should be understood that "vigorous" as used herein means rubbing or massaging of the scalp, whether by hand or by mechanical means, such as a brush.

What is claimed is:

1. In a process for dyeing hair on a live head wherein the hair is treated with metal ion in a pretreatment step to accelerate subsequent dyeing of the hair and the treated hair is then subjected to an oxidative or autooxidative dyeing step, wherein the improvement comprises,
   (a) between the pretreatment step and the dyeing step the scalp of said live head is subjected to vigorous massage, rubbing, combing or brushing, for a time sufficient to reduce staining of the scalp occasioned by the dyeing step; or
   (b) sufficient time is permitted to elapse between the pretreatment step and the dyeing step to reduce staining of the scalp occasioned by the dyeing step; or
   (c) between the pretreatment step and the dyeing step the scalp of said live head is subjected to vigorous massage, rubbing, combing or brushing and time is permitted to elapse between the pretreatment step and the dyeing step, the duration of the massage rubbing, combing or brushing coupled with the duration of the elapsed time between the pretreatment and dyeing steps being sufficient to reduce staining of the scalp occasioned by the dyeing step; and wherein at least 24 hours is permitted to elapse between the pretreatment step and the dyeing step.

2. The process, as claimed in claim 1, wherein at least 48 hours is permitted to elapse between the pretreatment step and the dyeing step.

3. The process, as claimed in claim 1, wherein from 24 to 72 hours is permitted to elapse between the pretreatment step and the dyeing step.

4. The process, as claimed in claim 1, wherein at least 48 to 72 hours is permitted to elapse between the pretreatment step and the dyeing step.

* * * * *